(12) United States Patent
Lee et al.

(10) Patent No.: US 11,311,854 B2
(45) Date of Patent: Apr. 26, 2022

(54) METHOD FOR PREPARING BIODEGRADABLE MICROSPHERES HAVING IMPROVED STABILITY AND STORAGE STABILITY

(71) Applicant: G2GBIO, INC., Daejeon (KR)

(72) Inventors: Heeyong Lee, Daejeon (KR); Eunyoung Seol, Daejeon (KR); Kwonhyeok Yoon, Daejeon (KR)

(73) Assignee: G2GBIO, INC., Daejeon (KR)

( * ) Notice: Subject to any disclaimer, the term of this patent is extended or adjusted under 35 U.S.C. 154(b) by 2 days.

(21) Appl. No.: 16/495,825

(22) PCT Filed: Nov. 30, 2018

(86) PCT No.: PCT/KR2018/015121
§ 371 (c)(1),
(2) Date: Sep. 19, 2019

(87) PCT Pub. No.: WO2019/108030
PCT Pub. Date: Jun. 6, 2019

(65) Prior Publication Data
US 2020/0298196 A1    Sep. 24, 2020

(30) Foreign Application Priority Data
Nov. 30, 2017    (KR) .................. 10-2017-0163105

(51) Int. Cl.
*B01J 13/12*   (2006.01)
*A61K 9/16*    (2006.01)
(Continued)

(52) U.S. Cl.
CPC ............. *B01J 13/12* (2013.01); *A61K 9/1694* (2013.01); *C08L 67/04* (2013.01); *A61K 45/06* (2013.01);
(Continued)

(58) Field of Classification Search
None
See application file for complete search history.

(56) References Cited

U.S. PATENT DOCUMENTS 5,945,126 A    8/1999   Thanoo et al.
2009/0162407 A1   6/2009   Biggs et al.
(Continued)

FOREIGN PATENT DOCUMENTS

CN    1426433    6/2003
CN    1430506    7/2003
(Continued)

OTHER PUBLICATIONS

EPO, Extended European Search Report of EP 18883786.8 dated Dec. 14, 2020.
(Continued)

*Primary Examiner* — Jeffrey D Washville
(74) *Attorney, Agent, or Firm* — Lex IP Meister, PLLC

(57) ABSTRACT

The present invention relates to a method for producing biodegradable microspheres having improved safety and storage stability, and a method for producing the same. The present invention provides a method for preparing said biodegradable microspheres while minimizing the morphological changes of microspheres and significantly reducing residual solvents.

17 Claims, 5 Drawing Sheets

Example 1-1

Comparative Example 1

(51) Int. Cl.
   *C08L 67/04* (2006.01)
   *A61K 45/06* (2006.01)
(52) U.S. Cl.
   CPC ....... *C08L 2201/06* (2013.01); *C08L 2203/02* (2013.01)

(56) References Cited

U.S. PATENT DOCUMENTS

| | | | |
|---|---|---|---|
| 2009/0269414 | A1 | 10/2009 | Lee et al. |
| 2010/0086597 | A1* | 4/2010 | Woo ................. A61K 38/31 424/486 |

FOREIGN PATENT DOCUMENTS

| | | |
|---|---|---|
| CN | 1798546 | 7/2006 |
| CN | 100571682 | 12/2009 |
| CN | 101657190 | 2/2010 |
| CN | 101693179 | 4/2010 |
| CN | 102137657 | 7/2011 |
| CN | 102159192 | 8/2011 |
| CN | 102440964 | 5/2012 |
| CN | 102516565 | 6/2012 |
| CN | 102670518 | 9/2012 |
| CN | 103386118 | 11/2013 |
| CN | 103462901 | 12/2013 |
| CN | 104055738 | 9/2014 |
| CN | 105308101 | 2/2016 |
| CN | 105338966 | 2/2016 |
| EP | 1629833 | 3/2006 |
| EP | 2982367 | 2/2016 |
| EP | 3031449 | 6/2016 |
| KR | 10-0722607 | 5/2007 |
| KR | 10-2008-0094616 | 10/2008 |
| KR | 10-2010-0026384 | 3/2010 |
| KR | 10-2010-0101190 | 9/2010 |
| KR | 10-1105292 | 1/2012 |
| KR | 10-2014-0115206 | 9/2014 |
| KR | 10-2014-0120496 | 10/2014 |
| KR | 10-1583351 | 1/2016 |
| KR | 10-2016-0019020 | 2/2016 |
| KR | 10-1738127 | 5/2017 |
| RU | 2326655 | 6/2008 |
| RU | 2016101418 | 7/2017 |
| WO | 01-83594 | 11/2001 |
| WO | 01-083594 | 11/2001 |
| WO | 02-49620 | 6/2002 |
| WO | 02-049620 | 6/2002 |
| WO | 2013-005094 | 1/2013 |
| WO | 2014-202214 | 12/2014 |

OTHER PUBLICATIONS

LuanHan-Sen et al., "Removal of Residual Dichloromethane in Naltrexone Microspheres by Reduced Pressure Heating Method", Chinese Journal of Pharmaceuticals 2005, 36(9).

SIPO, Office Action of CN 201880037391.0 dated May 7, 2021.

Bhavna et al., "Preparation, characterization, in vivo biodistribution and pharmacokinetic studies of donepezil-loaded PLGA nanoparticles for brain targeting", Drug Development and Industrial Pharmacy, Early Online: 1-10, 2013.

Pengcheng Zhang et al., "In vitro and in vivo evaluation of donepezil-sustained release microparticles for the treatment of Alzheimer's disease", Biomaterials, 28(2007) pp. 1882~1888.

"Evonik RESOMER RG 757 S Ester", http://www.matweb.com/search/datasheet.aspx?matguid=b25645f9122a46d480467d885f59fb6a&ckck=1.

Evonik RESOMER product brochure, http://healthcare.evonik.com/sites/lists/NC/DocumentsHC/Evonik_RESOMER_product_brochure.pdf.

* cited by examiner

[Fig. 1a]
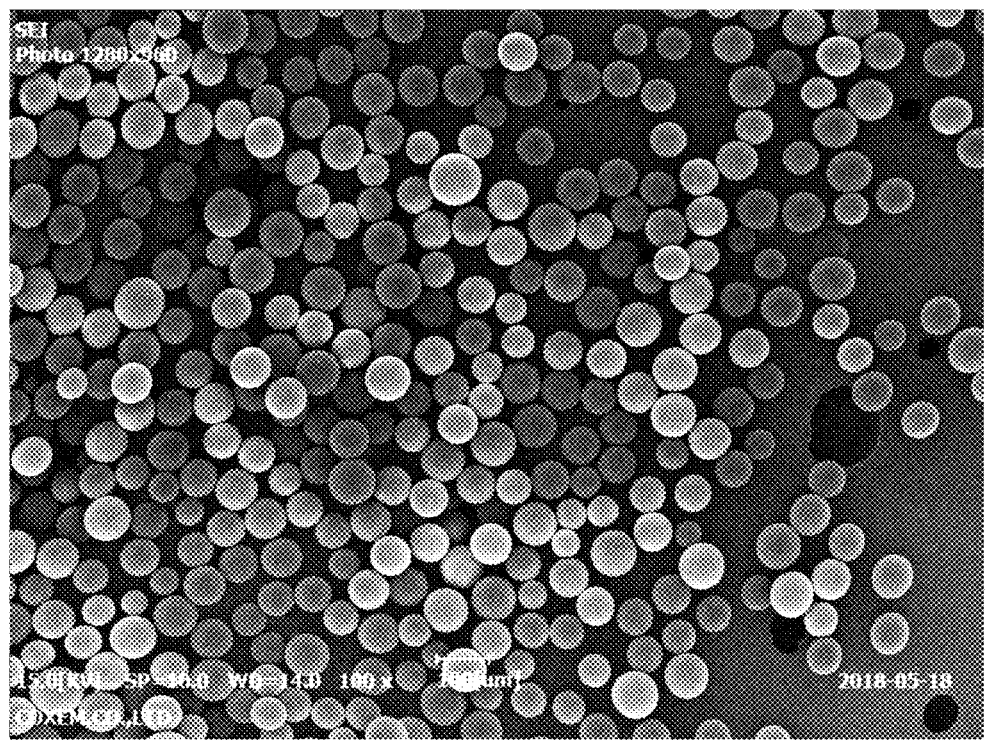
Example 1-1

[Fig 1b]
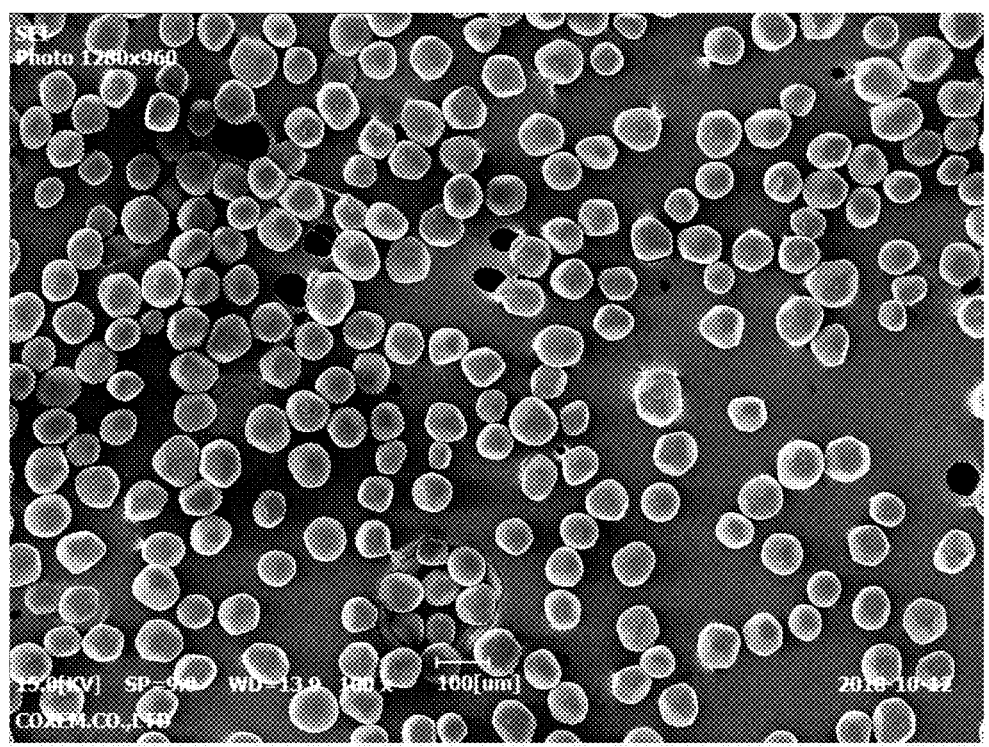
Comparative Example 1

[Fig. 1c]
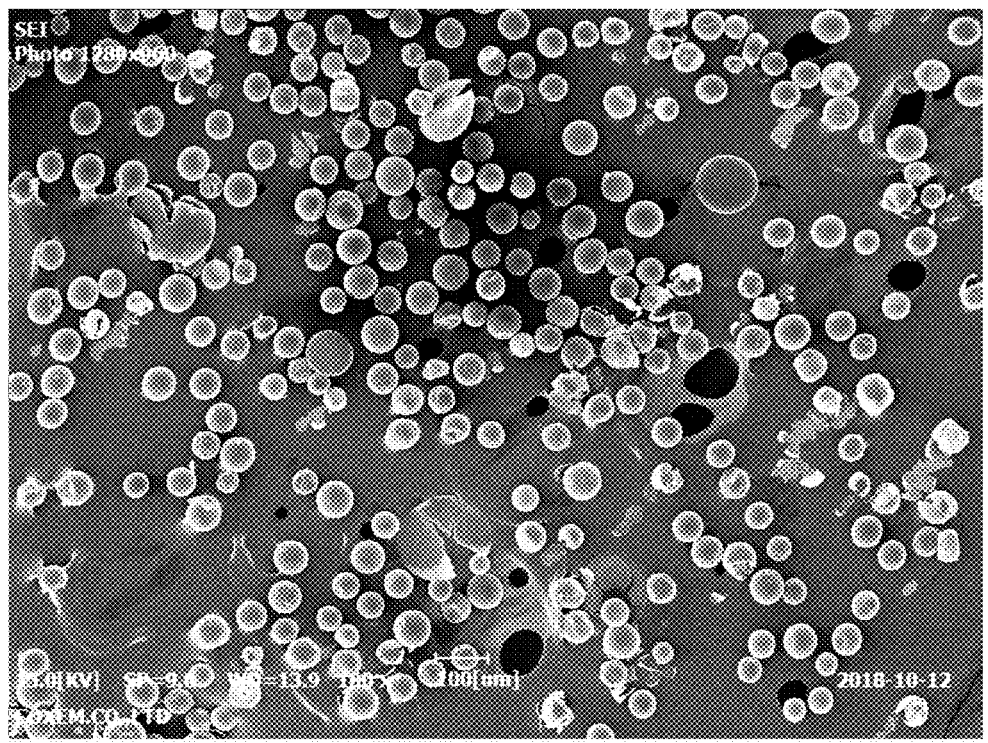
Comparative Example 2

[Fig. 1d]
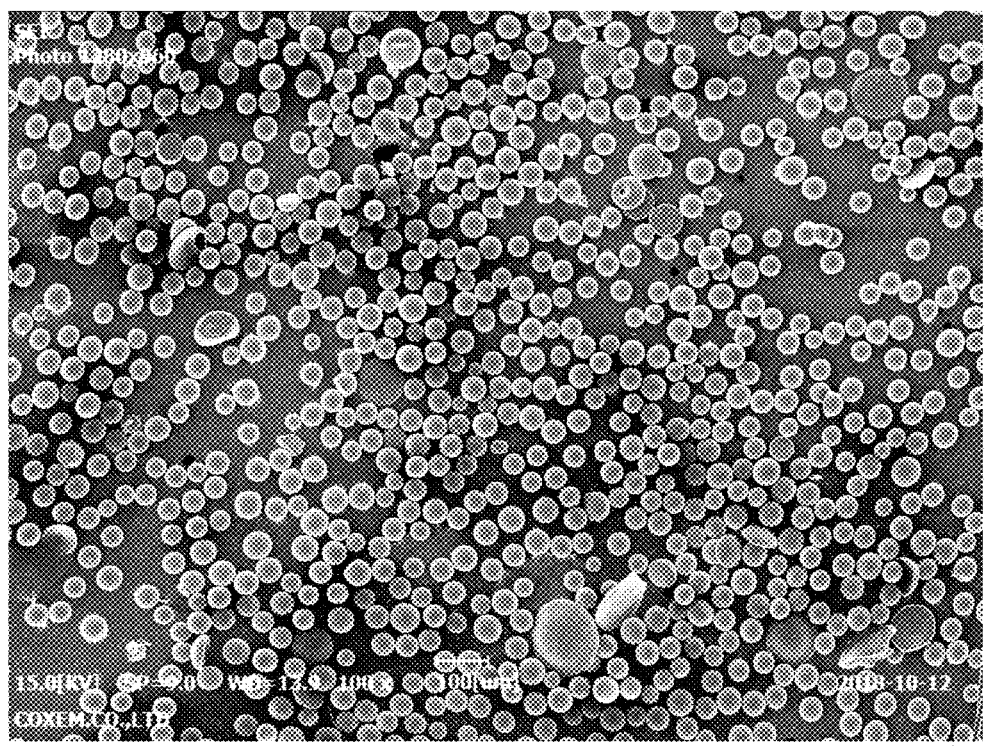
Example 5

[Fig. 1e]
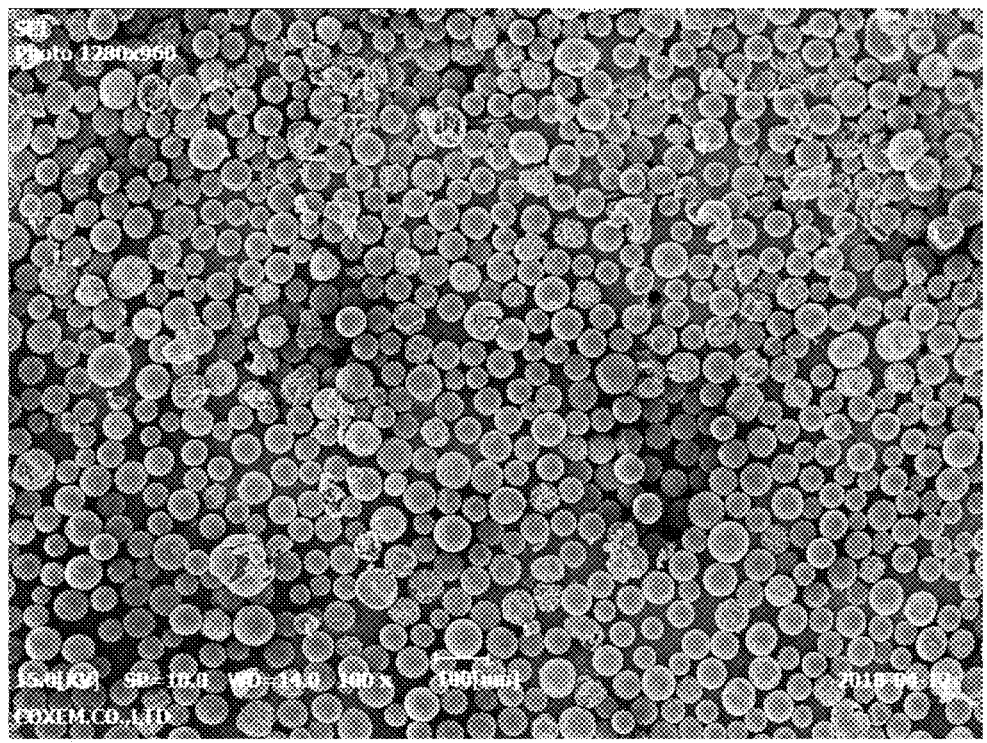
Comparative Example 3

METHOD FOR PREPARING BIODEGRADABLE MICROSPHERES HAVING IMPROVED STABILITY AND STORAGE STABILITY

CROSS REFERENCE WITH RELATED APPLICATION (S)

This application claims the benefit of priority based on Korean Patent Application No. 10-2017-0163105 dated Nov. 30, 2017, and all the contents disclosed in the literature of that Korean patent application are incorporated as part of this specification.

TECHNICAL FIELD

The present invention relates to a method for producing biodegradable microspheres, and more particularly, to a method for producing biodegradable microspheres having high safety by remarkably lowering the residual solvent, less deformations of microspheres, and improved storage stability.

RELATED ART

The biodegradable polymer can be prepared in the form of microspheres (e.g., particles having an average particle size in the nanometer to millimeter range, particularly 1 to 500 μm, particularly 10 to 150 μm) by various known techniques. The biodegradable polymeric microspheres can be used as particle fillers for improving facial wrinkles by themselves and are well used for the purpose of providing sustained or delayed release of a drug or other active agent by encapsulating said drug or other active agent. The most frequently used method for preparing said biodegradable polymer microsphere is dissolving the biodegradable polymer, or the biodegradable polymer and the substance (drug or other active agent) to be encapsulated in said polymer in a solvent then dispersing or emulsifying the resulting solution in an aqueous solution. The solvent is then removed from the microspheres to obtain the final microsphere product. Toxic solvents such as dichloromethane or chloroform are often used to dissolve biodegradable polymers and active agents in the microsphere production process according to the known art. Residues of these toxic solvents in the final product are undesirable because of their general toxicity and potential carcinogenic effects. Also, a mixture of various kinds of organic solvents is used to homogeneously dissolve the biodegradable polymer and the active agent simultaneously. This solvent mixture is dispersed in an aqueous solution to form an emulsion and then extracted and evaporated into an aqueous solution layer according to the solubility of each solvent in an aqueous solution, the affinity to the biodegradable polymer, etc. However, it has been found that the mixture of such organic solvents is not sufficiently removed during the production of microspheres according to the known prior art, and the residual solvent adversely affect the stability of the final product, such as promoting the decomposition of the polymer during the storage period of the finally produced microspheres. Accordingly, there is a need to develop a biodegradable polymer microsphere production method capable of increasing the shelf life of a product by reducing the residual amount of toxic solvent and organic solvent mixture.

DISCLOSURE

Technical Problem

Accordingly, the present invention has been made to solve the above mentioned problem of the conventional art. Thus, an object of the present invention is to provide a method for producing biodegradable microspheres having high safety by remarkably lowering the residual solvent, less deformations of microspheres, and improved storage stability.

Technical Solution

As one aspect to achieve such a purpose, the present invention relates to a method for preparing biodegradable microspheres comprising:

(a) forming a biodegradable polymer solution by dissolving a biodegradable polymer alone; or a biodegradable polymer and a drug in an organic solvent;

(b) uniformly mixing the biodegradable polymer solution prepared in the step (a) in an aqueous solution containing a surfactant, to form an emulsion containing the biodegradable polymer solution as a dispersed phase and an aqueous solution containing the surfactant as a continuous phase;

(c) extracting and evaporating the organic solvent from the dispersed phase in the emulsion of step (b) to the continuous phase to produce microspheres, wherein a part of the continuous phase containing the extracted organic solvent is removed, while a new continuous phase is supplied; and (d) recovering the microspheres from the continuous phase containing the produced microspheres of step (c).

Advantageous Effects

In the production of a biodegradable polymer microsphere containing a biodegradable polymer itself or a biodegradable microsphere containing a biodegradable polymer and a physiologically active drug, it is very important to minimize the residual amount of toxic solvent or organic solvent mixture remaining in the microsphere. The present invention provides a method for effectively preparing biodegradable microspheres having high safety and excellent storage stability by forming an emulsion and then removing a part of a continuous phase comprising an extracted the organic solvent from the dispersed phase, while supplying a new aqueous solution for replacing said continuous phase. Thus, it is possible to quickly and easily remove the residual organic solvent in the microspheres while minimizing morphological changes of the microspheres and the molecular weight reduction due to the hydrolysis of the biodegradable polymer in the microspheres.

BRIEF DESCRIPTION OF THE DRAWINGS

FIG. 1a is a scanning electron microscope (SEM) photograph for analysis of morphological characterization of the microspheres prepared in Example 1-1 of the present invention, confirming that most microspheres maintain the complete spherical morphology.

FIG. 1b is a SEM photograph for analysis of morphological characterization of the microspheres prepared in Comparative Example 1 (when the exchange time of the continuous phase solvent is faster than the time of the microsphere surface hardening), confirming that the microspheres cannot maintain the spherical shape.

FIG. 1c is a photograph of the microspheres prepared in Comparative Example 2 (when all the continuous phase solvent is removed) for analysis of morphological characterization, and the particle shape of the microspheres was confirmed to be changed by the scanning electron microscope.

FIG. 1d is a photograph of the microspheres prepared in Example 5 (when the continuous phase solvent contains an appropriate amount of ethyl alcohol) for analysis of morphological characterization using a SEM, confirming that most microspheres maintain the complete spherical morphology.

FIG. 1e is a photograph of the microspheres prepared in Comparative Example 3 (when continuous phase solvent contains 50% (v/v) or more ethyl alcohol) prepared in Comparative Example 3), for analysis of morphological characterization using a SEM, which shows the morphology of the microspheres was deformed by the abrupt removal of dichloromethane.

Hereinafter, the present invention will be described in more detail.

The present invention relates to a method for producing a microsphere by preparing a biodegradable polymer solution comprising a biodegradable polymer and an organic solvent as a dispersed phase, preparing an emulsion containing a surfactant as a continuous phase, extracting and evaporating the organic solvent from the dispersed phase into a continuous phase, wherein a part of the continuous phase comprising the extracted organic solvent from the dispersed phase is removed from the emulsion system, while supplying a new aqueous solution containing a surfactant to the emulsion system so as to replace said removed continuous phase, to provide biodegradable microspheres having reduced deformation of microspheres and improved storage stability.

As one embodiment of the present invention, the present invention relates to a method for preparing biodegradable microspheres comprising:

(a) forming a biodegradable polymer solution by dissolving a biodegradable polymer alone; or a biodegradable polymer and a drug in an organic solvent;

(b) uniformly mixing the biodegradable polymer solution prepared in the step (a) in an aqueous solution containing a surfactant, to form an emulsion containing the biodegradable polymer solution as a dispersed phase and an aqueous solution containing the surfactant as a continuous phase;

(c) extracting and evaporating the organic solvent from the dispersed phase in the emulsion of step (b) to the continuous phase to produce microspheres, wherein a part of the continuous phase containing the extracted organic solvent is removed, while a new continuous phase is supplied; and (d) recovering the microspheres from the continuous phase containing the produced microspheres of step (c).

Hereinafter, a method for producing the biodegradable polymer microspheres of the present invention will be described in detail.

As used herein, the term "solvent extraction and evaporation method" refers to a method in which a biodegradable polymer solution prepared by dissolving a biodegradable polymer alone, or a mixture of a biodegradable polymer and a drug in an organic solvent, is added to a continuous phase in the form of an aqueous solution containing a surfactant, extracting and evaporating the organic solvent from the dispersed phase of the emulsion into a continuous phase to form microspheres and recovering microspheres from the continuous phase to produce biodegradable polymer microspheres.

The preparation method of the present invention comprises (a) dissolving a biodegradable polymer alone or a mixture of a biodegradable polymer and a drug in an organic solvent to form a biodegradable polymer solution.

The step (a) may comprise a process of forming a biodegradable polymer solution by dissolving a biodegradable polymer in an organic solvent to form a biodegradable polymer solution, or a process of dissolving a biodegradable polymer and a drug simultaneously in an organic solvent mixture to form a drug-containing biodegradable polymer solution.

The weight average molecular weight of the biodegradable polymer is not particularly limited, but the lower limit may be 5,000 or more, preferably 10,000 or more, and the upper limit may be 500,000 or less, preferably 200,000 or less.

The type of the biodegradable polymer is not particularly limited, but polyesters may be preferably used. In particular, the biodegradable polymer may be selected from the group consisting of polylactide, polyglycolide, poly(lactide-co-glycolide), poly(lactide-co-glycolide) glucose, polycaprolactone, and mixtures thereof. More preferably, polylactide, poly(lactide-co-glycolide) and polycaprolactone may be used.

When poly(lactide-co-glycolide) is used as the biodegradable polymer, the molar ratio of lactic acid to glycolic acid (lactic acid:glycolic acid) in the copolymer may be 99:1 to 50:50, preferably 50:50, 75:25, or 85:15. Examples of commercially available biodegradable polymers that can be used in the present invention include Resomer series of Evonik, e.g., RG502H, RG503H, RG504H, RG502, RG503, RG504, RG653H, RG752H, RG752S, RG755S, RG756S, RG858S, R202H, R203H, R205H, R202S, R203S and R205S, PDL 02A, PDL 02, PDL 04, PDL 05, PDLG 7502A, PDLG 7502, PDLG 7507, PDLG 5002A, PDLG 5002, PDLG 5004A, PDLG 5004, PDLG 5010, PL 10, PL 18, PL 24, PL 32, PL 38, PDL 20, PDL 45, PC 02, PC 04, PC 12, PC 17 and PC 24 of Corbion.

In one specific embodiment, Resomer R203H, RG502H, RG653H, RG752H, RG757S, RG858S, R202H and R205S, and Purasorb PC 04 were used in order to prepare the microspheres according to the present invention.

The drug used in the step (a) is not particularly limited, and examples thereof include a dementia treatment agent; a therapeutic agent for Parkinson's disease; anticancer agents; antipsychotics such as anxiolytics, antidepressants, nervous stabilizers, and psychotropic agents; a cardiovascular therapeutic agent such as a therapeutic agent for hyperlipidemia, a therapeutic agent for hypertension, a therapeutic agent for hypotension, an antithrombotic agent, a vasodilator and an arrhythmic remedy; antiepileptics; gastrointestinal therapeutic agents such as anti-ulcer agents; a therapeutic agent for rheumatic diseases; antispasmodics; antitubercular drugs; muscle relaxants; a therapeutic agent for osteoporosis; drugs for erectile dysfunction; hematostatic agent; hormones such as sex hormones and the like; antidiabetic agents; antibiotics; antifungal agents; antiviral agents; antipyretic, analgesic and anti-inflammatory drugs; autonomic regulators; corticosteroids; diuretics; painkiller; anesthetic; antihistamines; anti-protozoal agent; antianemics; anti-asthmatics; anticonvulsants; antidote; anti-migraine agent; antiemetics; antiparkinson drug; antiepileptic agents; antiplatelet agents; antitussives & expectorants; bronchodilator; cardiotonics; immunomodulators; protein drugs; gene drug; and a mixture thereof. Preferably, the drug may be selected from the group consisting of the therapeutic agent for dementia, a drug for Parkinson's disease, anticancer agent, antipsychotic drug, antihyperlipidemia agent, antihypertension agent, antiepileptic agent, gastrointestinal therapeutic agent, antirheumatic drug, antispasmodic drug, antitubercular drugs, muscle relaxant, anti-arrhythmic agent, a therapeutic agent for osteoporosis, a therapeutic agent for erectile dysfunction, a hemostatic agent, an antiviral agent, a hormone agent, an antibiotics, antidiabetics, an antifungal agent, an antithrombotic agent, an antipyretic analgesic and anti-inflammatory agent and a mixture thereof.

Non-limiting examples of the above-mentioned drugs includes donepezil, memantine, rivastigmine, entecavir, lamivudine, rotigotine, ropinirole, bupivacaine, ropivacaine, meloxicam, buprenorphine, fentanyl, granisetron, triamcinolone, cytarabine, carmustine, tamsulosin, polmacoxib, testosterone, estradiol, risperidone, paliperidone, olanzapine, aripiprazole, goserelin, leuprolide, triptorelin, buserelin, nafarelin, deslorelin, octreotide, pasireotide, lanreotide, vapreotide, exenatide, liraglutide, lixisenatide, semaglutide and salts or a mixture thereof.

In the step (a), the solvent used to dissolve the biodegradable polymer preferably has a property not to be miscible with water. Owing to the property that the organic solvent is not miscible with water, the emulsion can be formed by homogeneously mixing the biodegradable polymer solution in the continuous phase in the step (b) to be described later. The example of the solvent for dissolving the biodegradable polymer is not particularly limited, but is preferably one or more solvent selected from the group consisting of dichloromethane, chloroform, ethyl acetate, acetone, acetonitrile, dimethyl sulfoxide, dimethylformamide, methyl ethyl ketone, acetic acid, methyl alcohol, ethyl alcohol, propyl alcohol, benzyl alcohol and a mixed solvent thereof, more preferably dichloromethane, ethyl acetate or a mixed solvent thereof.

The preparation method of the present invention comprises step (b) uniformly mixing the biodegradable polymer solution prepared in the step (a) in an aqueous solution containing a surfactant, to form an emulsion containing the biodegradable polymer solution as a dispersed phase and an aqueous solution containing the surfactant as a continuous phase.

For homogeneously mixing an aqueous solution containing a biodegradable polymer solution and a surfactant in the step (b), various mixing methods may be used, and non-limiting examples thereof is a high-speed mixer, an inline mixer, a membrane emulsion method or a microfluidic emulsion method.

When an emulsion containing an aqueous solution containing the biodegradable polymer solution and the surfactant is formed as in the step (b), the biodegradable polymer solution is homogeneously dispersed in the aqueous solution to form a dispersed phase in the form of droplets.

Therefore, the aqueous solution containing the surfactant as the continuous phase used in the step (b) is not miscible with the organic solvent in the biodegradable polymer solution as dispersed phase.

The surfactant used in the step (b) is not particularly limited and any type of surfactant may be used as long as helping the biodegradable polymer solution to form a stable liquid droplet dispersed phase in a continuous liquid phase. The surfactant is preferably selected from the group consisting of methylcellulose, polyvinylpyrrolidone, carboxymethylcellulose, lecithin, gelatin, polyvinyl alcohol, polyoxyethylene sorbitan fatty acid esters, polyoxyethylene castor oil derivatives and mixtures thereof. Also, most preferably polyvinyl alcohol may be used.

In step (b), the content of the surfactant in the aqueous solution containing the surfactant is 0.01% (w/v) to 20% (w/v) based on the total volume of the aqueous solution containing the surfactant, preferably 0.1% (w/v) to 5% (w/v). If the content of the surfactant is less than 0.01% (w/v), a dispersed phase in the form of a droplet in the aqueous solution or an emulsion may not be formed. If the content of the surfactant exceeds 20% (w/v), it is difficult to remove the surfactant after the microspheres are formed in the aqueous solution due to the excessive amount of the surfactant.

Furthermore, in a preferred embodiment, the continuous phase used in step (b) may further comprise one or more solvents selected from a group consisting of methyl alcohol, ethyl alcohol, propyl alcohol and ethyl acetate to control the extraction rate of the organic solvent from the emulsion as well as water and the surfactant. It is preferable that said solvent may be contained in an amount of 0.1% (v/v) to 40% (v/v) based on the total volume of the continuous phase.

The method of the present invention comprises a step (c) extracting and evaporating the organic solvent from the dispersed phase in the emulsion of step (b) to the continuous phase to produce microspheres, wherein a part of the continuous phase containing the extracted organic solvent is removed, while a new continuous phase is supplied into the emulsion.

In the step (c), when the emulsion containing the biodegradable polymer solution (dispersed phase) in droplet form and the continuous phase is maintained or stirred at a temperature lower than the boiling point of the organic solvent for a predetermined time, for example, 2 to 48 hours, the organic solvent can be extracted from the biodegradable polymer solution in a droplet form (a dispersed phase) into the continuous phase. Some of the organic solvent extracted to the continuous phase can be evaporated from the surface of the continuous phase containing the produced microspheres. As the organic solvent is extracted from the biodegradable polymer solution (dispersed phase) in the droplet form and evaporated, the dispersed phase in the droplet form can be solidified to form microspheres.

In the conventional method for producing a microsphere using a solvent extraction and evaporation method, heat is sometimes applied for a long time in order to sufficiently remove the organic solvent from the dispersed phase in the droplet form, and the heat degrades the biodegradable polymer, thereby lowering the molecular weight of the biodegradable polymer.

However, in the present invention, in the step (c), a part of the continuous phase containing the organic solvent extracted from the dispersed phase is removed and a new aqueous solution containing a surfactant replacing the removed continuous phase is supplied into the emulsion, thereby the residual amount of the organic solvent can be efficiently minimized by sufficiently extracting the organic solvent into a continuous phase and evaporating.

The present invention is characterized in that only a part of the continuous phase is removed and a new aqueous solution comprising a surfactant is supplied into the emulsion so that the solvent extraction process from the dispersed phase can be continuously performed. Preferably, exchange time for the continuous phase is more than 5 minutes, more preferably 10 minutes to 60 minutes from the time at which the surface of the microspheres starts to harden. When the continuous phase is exchanged faster than the above time, the microspheres cannot maintain the spherical shape and can be deformed.

In the step (c), removing a part of the continuous phase and supplying a new aqueous solution comprising a surfactant may be carried out by way of removing a part of the continuous phase in advance, then supplying the new aqueous solution as much as the continuous phase is removed.

When the continuous phase is discontinuously removed, it is preferred that (i) 40% (v/v) to 99% (v/v) of the continuous phase, or (ii) the rest of the continuous phase except for one (1) times of weight of the microspheres is removed from the emulsion system. If the continuous phase is removed beyond the above range (for example, the removal amount is less than 99% (v/v) or half (0.5) of the microsphere weight), the form of the produced microspheres may be deformed. Also, when 35% (v/v) or less of the continuous phase of 35% (v/v) or less is removed, the removal of the organic solvent may not be effective.

When removing a part of the continuous phase, the initially formed microspheres as a dispersed phase may be retained by using a filter or the like and only a part of continuous phase may be removed by using a peristaltic pump or the like.

As another method for step (c), a method of continuously supplying a fresh aqueous solution comprising a surfactant while simultaneously removing a part of the continuous phase may be used.

Upon removal of the continuous phase, it may be removed at a rate of 2% (v/v) to 200% (v/v) relative to the total continuous phase volume per minute.

The aqueous solution containing the surfactant as a new continuous phase which is additionally supplied in the step (c) may comprise a water or a mixed solvent comprising (i) water and (ii) one or more selected from the group consisting of aliphatic alcohols having 1 to 4 carbon atoms (preferably, methyl alcohol, ethyl alcohol or propyl alcohol) and ethyl acetate in a predetermined amount. Also, it is preferable that the mixed solvent is contained in an amount of 0.1% (v/v) to 40% (v/v) based on the total volume of the continuous phase to be newly added.

By continuously removing the organic solvent extracted by the continuous phase substitution method of the step (c) of the present invention, the organic solvent can be efficiently extracted and the residual solvent can be minimized.

In order to further efficiently remove the organic solvent in step (c) of the present invention, heat may be applied for a certain period of time so as to keep the temperature of the continuous phase constant.

The method of the present invention comprises step (d) recovering the microspheres from the emulsion prepared in said step (c). Various known techniques may be used for recovering the microspheres, such as filtration or centrifugation.

In the method of the present invention, the residual surfactant may be removed through filtration and washing between step (c) and step (d), and the microspheres may be recovered by further filtration.

The washing step for removing the residual surfactant may be usually carried out using water, and the washing step may be repeated several times.

In the method of the present invention, after the step (d) or after the above filtration and washing step, the obtained microspheres may be dried using a conventional drying method to obtain finally dried microspheres.

Preferably, in the method of the present invention, the obtained microspheres may be suspended in a suspension after step (d) or after the filtration and washing step between steps (c) and (d), then may be filled into a pharmaceutically acceptable container, for example, disposable syringe or the like to obtain a final product.

The method described above allows to efficiently remove the residual solvent in the biodegradable microspheres, minimize the molecular weight reduction due to hydrolysis of the biodegradable polymer in the microsphere, and provide the biodegradable polymer microspheres having excellent safety and storage stability.

Preferably, when the microparticles are produced by the method according to the present invention, the residual solvent content in the dried microparticles after production is 1000 ppm or less, more preferably 600 ppm or less.

Hereinafter, the present invention will be described in more detail with reference to the following examples. However, the following examples are illustrative of the present invention, and the present invention is not limited to the following examples.

MODE FOR INVENTION

Example 1: Production of Microspheres Prepared by Different Continuous Phase Exchange Time 3.5 g of a biocompatible polymer Resomer R203H (manufacturer: Evonik, Germany; poly(D,L-lactide) Mw: 18,000 to 28,000) and 1.5 g of donepezil base (manufacturer: Neuland Laboratories, India) were dissolved in 9.2 g of dichloromethane (JT Baker, USA) to prepare a dispersed phase. The dispersed phase was prepared by stirring for 30 minutes or more for sufficient dissolution and then used. An aqueous solution of 1% (w/v) polyvinyl alcohol (viscosity: 4.8 to 5.8 mPa·s) was used as a continuous phase. A container including 460 mL of the continuous phase was connected to an emulsification apparatus equipped with a membrane having 40 μm diameter pores, while the above dispersed phase was simultaneously injected into the apparatus to produce the microsphere suspension. Then the resulting microsphere suspension was placed in a preparation vessel and stirred at 150 rpm.

The temperature of the membrane emulsification apparatus and the preparation vessel was maintained at 25° C. and the stirring was maintained for 15 minutes. 455 mL of the continuous phase was removed while 5 mL of the continuous phase (the same amount of total weight of the biodegradable polymer and donepezil base used in the dispersed phase preparation) was remained. Then, a new continuous phase solution was added into the apparatus in the same amount as the removed continuous phase. The organic solvent was removed while maintaining the temperature at 45° C. for 3 hours. After removal of the organic solvent, the temperature of the microsphere suspension was lowered to 25° C. The microsphere suspension was washed three times with deionized water to remove residual polyvinyl alcohol, and the resulting microspheres were lyophilized.

Example 1-1: Production of Microspheres Prepared by Different Continuous Phase Exchange Time 3.5 g of a biocompatible polymer Resomer R203H (manufacturer: Evonik, Germany) and 1.5 g of donepezil base (manufacturer: Neuland Laboratories, India) were dissolved in 9.2 g of dichloromethane (JT Baker, USA) to prepare a dispersed phase. The dispersed phase was prepared by stirring for 30 minutes or more for sufficient dissolution and then used. An aqueous solution of 1% (w/v) polyvinyl alcohol (viscosity: 4.8 to 5.8 mPa·s) was used as a continuous phase. A container including 460 mL of the continuous phase was connected to an emulsification apparatus equipped with a membrane having 40 μm diameter pores, while the above dispersed phase was simultaneously injected into the apparatus to produce the microsphere suspension. Then the resulting microsphere suspension was placed in a preparation vessel and stirred at 150 rpm.

The temperature of the membrane emulsification apparatus and the preparation vessel was maintained at 25° C. and the stirring was maintained for 30 minutes. 455 mL of the continuous phase was removed while 5 mL of the continuous phrase (the same amount of total weight of the biodegradable polymer and donepezil base used in the dispersed phase preparation) was remained. Then, a new continuous phase solution was added into the apparatus in the same amount as the removed continuous phase. The organic solvent was removed while maintaining the temperature at 45° C. for 3 hours. After removal of the organic solvent, the temperature of the microsphere suspension was lowered to 25° C. The microsphere suspension was washed three times with deionized water to remove residual polyvinyl alcohol, and the resulting microspheres were lyophilized.

Example 1-2: Production of Microspheres Prepared by Different Continuous Phase Exchange Time 3.5 g of a biocompatible polymer Resomer R203H (manufacturer: Evonik, Germany) and 1.5 g of donepezil base (manufacturer: Neuland Laboratories, India) were mixed with 9.2 g of dichloromethane (JT Baker, USA) to prepare a dispersed phase. The dispersed phase was prepared by stirring for 30 minutes or more for sufficient dissolution and then used. An aqueous solution of 1% (w/v) polyvinyl alcohol (viscosity: 4.8 to 5.8 mPa·s) was used as a continuous phase. A container including 460 mL of the continuous phase was connected to an emulsification apparatus equipped with a membrane having 40 μm diameter pores, while the above dispersed phase was simultaneously injected into the apparatus to produce the microsphere suspension. Then the resulting microsphere suspension was placed in a preparation vessel and stirred at 150 rpm.

The temperature of the membrane emulsification apparatus and the preparation vessel was maintained at 25° C. and the stirring was maintained for 60 minutes. 455 mL of the continuous phase was removed while 5 mL of the continuous phrase (the same amount of total weight of the biodegradable polymer and donepezil base used in the dispersed phase preparation) was remained. Then, a new continuous phase solution was added into the apparatus in the same amount as the removed continuous phase. The organic solvent was removed while maintaining the temperature at 45° C. for 3 hours. After removal of the organic solvent, the temperature of the microsphere suspension was lowered to 25° C. The microsphere suspension was washed three times with deionized water to remove residual polyvinyl alcohol, and the resulting microspheres were lyophilized.

Example 2: Preparation of Microspheres Prepared by Different Continuous Phase Exchange Amounts 3.5 g of a biocompatible polymer Resomer R203H (manufacturer: Evonik, Germany) and 1.5 g of donepezil base (manufacturer: Neuland Laboratories, India) were dissolved in 9.2 g of dichloromethane (JT Baker, USA). The dispersed phase was prepared by stirring for 30 minutes or more for sufficient dissolution and then used. An aqueous solution of 1% (w/v) polyvinyl alcohol (viscosity: 4.8 to 5.8 mPa·s) was used as a continuous phase. A container including 460 mL of the continuous phase was connected to an emulsification apparatus equipped with a membrane having 40 μm diameter pores, while the above dispersed phase was simultaneously injected into the apparatus to produce the microsphere suspension. Then the resulting microsphere suspension was placed in a preparation vessel and stirred at 150 rpm.

The temperature of the membrane emulsification apparatus and the preparation vessel was maintained at 25° C. and the stirring was maintained for 30 minutes. 230 mL of the continuous phase (50% of the total volume of the continuous phase) was removed and a new continuous phase solution was added into the apparatus in the same amount as the removed continuous phase (230 mL). The organic solvent was removed while maintaining the temperature at 45° C. for 3 hours. After removal of the organic solvent, the temperature of the microsphere suspension was lowered to 25° C. The microsphere suspension was washed three times with deionized water to remove residual polyvinyl alcohol, and the resulting microspheres were lyophilized.

Example 3 Preparation of Microspheres Using Ethyl Acetate

The dispersed phase was prepared by mixing 3.5 g of a biocompatible polymer, Resomer R203H (manufacturer: Evonik, Germany) and 1.5 g of donepezil base (manufacturer: Neuland Laboratories, India) with 10.5 g of ethyl acetate (Sigma Aldrich, USA). The dispersed phase was sufficiently dissolved by stirring for 30 minutes or more and then used. An aqueous solution of 1% (w/v) polyvinyl alcohol (viscosity: 4.8 to 5.8 mPa·s) was used as a continuous phase. A container including 530 mL of the continuous phase was connected to an emulsification apparatus equipped with a membrane having 20 μm diameter pores, while the above dispersed phase was simultaneously injected into the apparatus to produce the microsphere suspension. Then the resulting microsphere suspension was placed in a preparation vessel and stirred at 300 rpm.

The temperature of the membrane emulsification apparatus and the preparation vessel was maintained at 25° C. and the stirring was maintained for 30 minutes. 525 mL of the continuous phase was removed while 5 mL of the continuous phrase was remained. Then, a new continuous phase solution was added into the apparatus in the same amount as the removed continuous phase. The organic solvent was removed while maintaining the temperature at 45° C. for 3 hours. After removal of the organic solvent, the temperature of the microsphere suspension was lowered to 25° C. The microsphere suspension was washed three times with deionized water to remove residual polyvinyl alcohol, and the resulting microspheres were lyophilized.

Example 4: Production of Microspheres Using RG502H

The dispersed phase was prepared by mixing 3.5 g of a biocompatible polymer Resomer RG502H (manufacturer: Evonik, Germany; poly(D,L-lactide-co-glycolide) 50:50; Mw: 7,000 to 17,000) and a donepezil base (manufactured by Neuland Laboratories, India) with 7.8 g of dichloromethane (manufacturer: JT Baker, USA). The dispersed phase was sufficiently dissolved by stirring for 30 minutes or more and then used. An aqueous solution of 1% (w/v) polyvinyl alcohol (viscosity: 4.8-5.8 mPa·s) was used as a continuous phase. 1750 mL of the continuous phase was poured into the preparation vessel and stirred with high speed mixer (L4RT, Silverson, UK) at 3000 rpm, while injecting the dispersed phase at a flow rate of 7 mL per minute.

When the dispersed phase injection was completed, the suspension in the preparation vessel was maintained at 25° C. for 30 minutes while stirring at 200 rpm. 1745 mL of the continuous phase was removed, while remaining 5 mL of continuous phase. Then the same amount of new continuous phase solution was added into the preparation vessel. The organic solvent was removed while maintaining the temperature at 40° C. for 3 hours. After removal of the organic solvent, the temperature of the microsphere suspension was lowered to 25° C. The suspension comprising microspheres was washed three times with deionized water to remove residual polyvinyl alcohol, and the microspheres were lyophilized.

Example 4-1: Preparation of Microspheres Using RG653H 3.5 g of a biocompatible polymer Resomer RG653H (manufacturer: Evonik, Germany; poly(D,L-lactide-co-glycolide) 65:35; Mw: 24,000 to 38,000) and 1.5 g of a donepezil base (manufactured by Neuland Laboratories, India) were dissolved in 17.5 g of dichloromethane (JT Baker, USA) to prepare the dispersed phase. The dispersed phase was stirred for 30 minutes or more for sufficient dissolution and then used. An aqueous solution of 2% (w/v) polyvinyl alcohol (viscosity: 4.8 to 5.8 mPa·s) was used as a continuous phase. A container including 880 mL of the continuous phase was connected to an emulsification apparatus equipped with a membrane having 30 μm diameter pores, while the above dispersed phase was simultaneously injected into the apparatus to produce the microsphere suspension. Then the resulting microsphere suspension was placed in a preparation vessel and stirred at 180 rpm.

The temperature of the membrane emulsification apparatus and the preparation vessel was maintained at 25° C. and the stirring was maintained for 30 minutes. 875 mL of the continuous phase was removed, while remaining 5 mL of continuous phase. Then the same amount of new continuous phase solution was added into the preparation vessel. The organic solvent was removed while maintaining the temperature at 40° C. for 3 hours. After removal of the organic solvent, the temperature of the microsphere suspension was lowered to 25° C. The microsphere suspension was washed three times with deionized water to remove residual polyvinyl alcohol, and the resulting microspheres were lyophilized.

Example 4-2: Preparation of Microspheres Using RG752H Polymer 3.5 g of a biocompatible polymer Resomer RG752H (manufacturer: Evonik, Germany; poly(D,L-lactide-co-glycolide) 75:25, Mw: 4,000 to 15,000) and 1.5 g of a donepezil base (manufactured by Neuland Laboratories, India) were mixed with 10.0 g of dichloromethane (manufacturer: JT Baker, USA) to prepare the dispersed phase. The dispersed phase was sufficiently dissolved by stirring for 30 minutes or more and then used. An aqueous solution of 1% (w/v) polyvinyl alcohol (viscosity: 4.8-5.8 mPa·s) was used as a continuous phase. 500 mL of the continuous phase was poured into the preparation vessel and stirred with high speed mixer (L4RT, Silverson, UK) at 3000 rpm, while injecting the dispersed phase at a flow rate of 15 mL per minute.

When the dispersed phase injection was completed, the suspension in the preparation vessel was maintained at 25° C. for 30 minutes while stirring at 200 rpm. 495 mL of the continuous phase was removed, while remaining 5 mL of continuous phase. Then the same amount of new continuous phase solution was added into the preparation vessel. The organic solvent was removed while maintaining the temperature at 40° C. for 3 hours. After removal of the organic solvent, the temperature of the microsphere suspension was lowered to 25° C. The suspension comprising microsphere was washed three times with deionized water to remove residual polyvinyl alcohol, and the microspheres were lyophilized.

Example 4-3: Preparation of Microspheres Using RG757S 3.5 g of a biocompatible polymer Resomer RG757S (manufacturer: Evonik, Germany; poly(D,L-lactide-co-glycolide) 75; 25; Mw: 110,000 to 180,000) and 1.5 g of donepezil base (manufactured by Neuland Laboratories, India) were mixed with 26.9 g of dichloromethane (manufacturer: JT Baker, USA) to prepare the dispersed phase. The dispersed phase was sufficiently dissolved by stirring for 30 minutes or more and then used. An aqueous solution of 4% (w/v) polyvinyl alcohol (viscosity: 4.8-5.8 mPa·s) was used as a continuous phase. 1400 mL of the continuous phase was poured into the preparation vessel equipped with high speed mixer (L4RT, Silverson, UK) and stirred at 5000 rpm, while injecting the dispersed phase at a flow rate of 10 mL per minute.

When the dispersed phase injection was completed, the suspension in the preparation vessel was maintained at 25° C. for 30 minutes while stirring at 150 rpm. 1395 mL of the continuous phase was removed, while remaining 5 mL of continuous phase. Then the same amount of new continuous phase solution was added into the preparation vessel. The organic solvent was removed while maintaining the temperature at 40° C. for 3 hours. After removal of the organic solvent, the temperature of the microsphere suspension was lowered to 25° C. The suspension comprising microsphere was washed three times with deionized water to remove residual polyvinyl alcohol, and the microspheres were lyophilized.

Example 4-4: Preparation of Microspheres Using RG858S 3.5 g of a biocompatible polymer Resomer RG858S (manufacturer: Evonik, Germany; poly(D,L-lactide-co-glycolide) 85:15; MW: 190,000 to 240,000) and 1.5 g of donepezil base (manufactured by Neuland Laboratories, India) were mixed with 38.9 g of dichloromethane (manufacturer: JT Baker, USA) to prepare the dispersed phase. The dispersed phase was sufficiently dissolved by stirring for 30 minutes or more and then used. An aqueous solution of 2.5% (w/v) polyvinyl alcohol (viscosity: 4.8-5.8 mPa·s) was used as a continuous phase.

A container including 2000 mL of the continuous phase was connected to an emulsification apparatus equipped with a membrane having 20 μm diameter pores, while the above dispersed phase was simultaneously injected into the apparatus to produce the microsphere suspension. Then the resulting microsphere suspension was placed in a preparation vessel and stirred at 250 rpm.

The temperature of the membrane emulsification apparatus and the preparation vessel was maintained at 25° C. and the stirring was maintained for 30 minutes. 1995 mL of the continuous phase was removed while 5 mL of the continuous phrase was remained. Then, a new continuous phase solution was added into the apparatus in the same amount as the removed continuous phase. The organic solvent was removed while maintaining the temperature at 40° C. for 3 hours. After removal of the organic solvent, the temperature of the microsphere suspension was lowered to 25° C. The microsphere suspension was washed three times with deionized water to remove residual polyvinyl alcohol, and the resulting microspheres were lyophilized.

Example 4-5: Preparation of Microspheres Using R202H 3.5 g of a biocompatible polymer Resomer R202H (manufacturer: Evonik, Germany; poly(D,L-lactide) Mw: 10,000 to 18,000) and 1.5 g of donepezil base (manufactured by Neuland Laboratories, India) were mixed with 7.8 g of dichloromethane (manufacturer: JT Baker, USA) to prepare the dispersed phase. The dispersed phase was sufficiently dissolved by stirring for 30 minutes or more and then used. An aqueous solution of 2.5% (w/v) polyvinyl alcohol (viscosity: 4.8-5.8 mPa·s) was used as a continuous phase.

A container including 390 mL of the continuous phase was connected to an emulsification apparatus equipped with a membrane having 50 μm diameter pores, while the above dispersed phase was simultaneously injected into the apparatus to produce the microsphere suspension. Then the resulting microsphere suspension was placed in a preparation vessel and stirred at 250 rpm.

The temperature of the membrane emulsification apparatus and the preparation vessel was maintained at 25° C. and the stirring was maintained for 30 minutes. 385 mL of the continuous phase was removed while 5 mL of the continuous phrase was remained. Then, a new continuous phase solution was added into the apparatus in the same amount as the removed continuous phase. The organic solvent was removed while maintaining the temperature at 40° C. for 3 hours. After removal of the organic solvent, the temperature of the microsphere suspension was lowered to 25° C. The microsphere suspension was washed three times with deionized water to remove residual polyvinyl alcohol, and the resulting microspheres were lyophilized.

Example 4-6: Preparation of Microspheres Using R205S 3.5 g of a biocompatible polymer Resomer R205S (manufacturer: Evonik, Germany; poly(D,L-lactide) Mw: 58000 to 89000) and 1.5 g of Donepezil base (manufacturer: Neuland Laboratories, India) were dissolved in 17.5 g of dichloromethane Manufactured by JT Baker, USA) to form the dispersed phase. The dispersed phase was sufficiently dissolved by stirring for 30 minutes or more and then used. As a continuous phase, an aqueous solution of 1% polyvinyl alcohol (viscosity: 4.8-5.8 mPa·s) was used, and a container including 880 mL of the continuous phase was connected to an emulsification apparatus equipped with a membrane having 40 μm diameter pores, while injecting the dispersed phase to form the suspension of the microspheres. The suspension of the microspheres was placed in a preparation vessel and stirred at 100 rpm.

The temperature of the membrane emulsification apparatus and the preparation vessel was maintained at 25° C. and the stirring was maintained for 30 minutes. 875 mL of the continuous phase was removed while 5 mL of the continuous phrase was remained. Then, a new continuous phase solution was added into the apparatus in the same amount as the removed continuous phase. The organic solvent was removed while maintaining the temperature at 40° C. for 3 hours. After removal of the organic solvent, the temperature of the microsphere suspension was lowered to 25° C. The microsphere suspension was washed three times with deionized water to remove residual polyvinyl alcohol, and the resulting microspheres were lyophilized.

Example 4-7: Production of Microspheres Using PC04

The dispersed phase was prepared by mixing 5 g of a biocompatible polymer, Purasorb PC04 (manufacturer: Corbion, Netherlands; polycaprolactone; Mw: 28000 to 38000) with 20.0 g of dichloromethane (manufacturer: J.T Baker, USA). The dispersed phase was sufficiently dissolved by stirring for 30 minutes or more before use. The continuous phase was an aqueous solution of 1% (w/v) polyvinyl alcohol (viscosity: 4.8-5.8 mPa·s), and a container including 700 mL of the continuous phase was connected to an emulsification apparatus equipped with a membrane having 40 μm diameter pores, while simultaneously injecting the prepared dispersed phase to produce the microspheres in suspension. The resulting microsphere suspension was placed in a preparation vessel and stirred at 150 rpm.

The temperature of the membrane emulsification apparatus and the preparation vessel was maintained at 25° C. and the stirring was maintained for 30 minutes. 455 mL of the continuous phase was removed while 695 mL of the continuous phrase was remained. Then, a new continuous phase solution was added into the apparatus in the same amount as the removed continuous phase. The organic solvent was removed while maintaining the temperature at 40° C. for 3 hours. After removal of the organic solvent, the temperature of the microsphere suspension was lowered to 25° C. The microsphere suspension was washed three times with deionized water to remove residual polyvinyl alcohol, and the resulting microspheres were lyophilized.

Example 5 Preparation of Microspheres Using Continuous Phase Comprising Ethyl Alcohol The dispersed phase was prepared by mixing 3.5 g of a biocompatible polymer Resomer R203H (manufacturer: Evonik, Germany) and 1.5 g of donepezil base (manufacturer: Neuland Laboratories, India) with 9.2 g of dichloromethane (manufacturer: J.T Baker, USA). The dispersed phase was sufficiently dissolved by stirring for 30 minutes or more and then used. As the continuous phase was an aqueous solution containing 1% (w/v) polyvinyl alcohol (viscosity: 4.8-5.8 mPa·s) and 30% (v/v) ethyl alcohol. A container including the continuous phase was connected to an emulsification apparatus equipped with a membrane having 40 μm diameter pores, while simultaneously injecting the prepared dispersed phase to produce the microspheres in suspension. The resulting microsphere suspension was placed in a preparation vessel and stirred at 200 rpm.

The temperature of the membrane emulsification apparatus and the preparation vessel was maintained at 25° C. When the dispersed phase injection was completed, stirring was maintained for 30 minutes. In this step, 455 mL of the remaining continuous phase was removed, while leaving 5 mL of continuous phase, and the same amount of new continuous phase solution was added. The organic solvent was removed while maintaining the temperature at 40° C. for 3 hours. After removal of the organic solvent, the temperature of the microsphere suspension was lowered to 25° C. The microsphere suspension was washed three times with deionized water to remove residual polyvinyl alcohol, and the microspheres were lyophilized.

Example 6: Preparation of Microspheres with a Process for Continuously Adding and Removing a Continuous Phase 3.5 g of a biocompatible polymer Resomer R203H (manufacturer: Evonik, Germany) and 1.5 g of Donepezil base (manufacturer: Neuland Laboratories, India) were mixed with 9.2 g of dichloromethane (manufacturer: J.T Baker, USA) to prepare the dispersed phase. The dispersed phase was sufficiently dissolved by stirring for 30 minutes or more and then used. An aqueous solution of 1% (w/v) polyvinyl alcohol (viscosity: 4.8-5.8 mPa·s) was used as a continuous phase. 460 mL of the continuous phase was poured into the preparation vessel equipped with high speed mixer (L4RT, Silverson, UK) and stirred at 2000 rpm, while injecting the dispersed phase at a flow rate of 10 mL per minute. The temperature of the membrane emulsification apparatus and the preparation vessel was maintained at 25° C. When the dispersed phase injection was completed, the continuous phase was removed at a flow rate of 13.8 mL per minute (3% of the total continuous phase volume) while injecting a new continuous phase at the same rate of removal for 1 hour. Then, the temperature of the apparatus was maintained at 45° C. for 3 hours. When the removal of the organic solvent was completed, the temperature of the microsphere suspension was lowered to 25° C. The suspension comprising microsphere was washed three times with deionized water to remove residual polyvinyl alcohol, and the microspheres were lyophilized.

Example 6-1: Preparation of Microspheres with a Process of Continuously Adding and Removing a Continuous Phase 3.5 g of a biocompatible polymer Resomer R203H (manufacturer: Evonik, Germany) and 1.5 g of Donepezil base (manufacturer: Neuland Laboratories, India) were mixed with 9.2 g of dichloromethane (manufacturer: J.T Baker, USA) to prepare the dispersed phase. The dispersed phase was sufficiently dissolved by stirring for 30 minutes or more and then used. An aqueous solution of 1% (w/v) polyvinyl alcohol (viscosity: 4.8-5.8 mPa·s) was used as a continuous phase. 460 mL of the continuous phase was poured into the preparation vessel equipped with high speed mixer (L4RT, Silverson, UK) and stirred at 2000 rpm, while injecting the dispersed phase at a flow rate of 10 mL per minute and maintaining the temperature of the preparation vessel to be 25° C. When the dispersed phase injection was completed, the continuous phase was removed at a flow rate of 27.6 mL per minute (6% of the total continuous phase volume) while injecting a new continuous phase at the same rate of removal for 1 hour. Then, the temperature of the preparation vessel was maintained at 45° C. for 3 hours. When the removal of the organic solvent was completed, the temperature of the microsphere suspension was lowered to 25° C. The suspension comprising microsphere was washed three times with deionized water to remove residual polyvinyl alcohol, and the microspheres were lyophilized.

Example 6-2: Preparation of Microspheres by Further Comprising a Step of Continuously Adding and Removing a Continuous Phase 3.5 g of a biocompatible polymer Resomer R203H (manufacturer: Evonik, Germany) and 1.5 g of donepezil base (manufacturer: Neuland Laboratories, India) were mixed with 9.2 g of dichloromethane (manufacturer: J.T Baker, USA) to form the dispersed phase. The dispersed phase was sufficiently dissolved by stirring for 30 minutes or more and then used. An aqueous solution of 1% (w/v) polyvinyl alcohol (viscosity: 4.8-5.8 mPa·s) was used as a continuous phase. 460 mL of the continuous phase was poured into the preparation vessel equipped with high speed mixer (L4RT, Silverson, UK) and stirred at 2000 rpm, while injecting the dispersed phase at a flow rate of 10 mL per minute and maintaining the temperature of the preparation vessel to be 25° C. When the dispersed phase injection was completed, the continuous phase was removed at a flow rate of 26.7 mL per minute (6% of the total continuous phase volume) while injecting a new continuous phase at the same rate of removal for 0.5 hour. Then, the temperature of the preparation vessel was maintained at 45° C. for 3 hours. When the removal of the organic solvent was completed, the temperature of the microsphere suspension was lowered to 25° C. The suspension comprising microsphere was washed three times with deionized water to remove residual polyvinyl alcohol, and the microspheres were lyophilized.

Example 6-3: Preparation of Microspheres with a Step of Continuously Adding and Removing a Continuous Phase 3.5 g of a biocompatible polymer Resomer R203H (manufacturer: Evonik, Germany) and 1.5 g of Donepezil base (manufacturer: Neuland Laboratories, India) were mixed with 9.2 g of dichloromethane (manufacturer: J.T Baker, USA) to form the dispersed phase. The dispersed phase was sufficiently dissolved by stirring for 30 minutes or more and then used. An aqueous solution of 1% (w/v) polyvinyl alcohol (viscosity: 4.8-5.8 mPa·s) was used as a continuous phase. 460 mL of the continuous phase was poured into the preparation vessel equipped with high speed mixer (L4RT, Silverson, UK) and stirred at 2000 rpm, while injecting the dispersed phase at a flow rate of 10 mL per minute and maintaining the temperature of the preparation vessel to be 25° C. When the dispersed phase injection was completed, the continuous phase was removed at a flow rate of 920 mL per minute (200% of the total continuous phase volume) while injecting a new continuous phase at the same rate of removal for 10 minutes. Then, the temperature of the preparation vessel was maintained at 45° C. for 3 hours. When the removal of the organic solvent was completed, the temperature of the microsphere suspension was lowered to 25° C. The suspension comprising microsphere was washed three times with deionized water to remove residual polyvinyl alcohol, and the microspheres were lyophilized.

Example 7: Preparation of Microspheres Comprising Rivastigmine

The dispersed phase was prepared by mixing 4.0 g of a biocompatible polymer, Resomer R203H (manufacturer: Evonik, Germany), and 1.0 g of rivastigmine base (manufacturer: Hwail Pharmaceutical Co., Ltd., Korea) with 10.0 g of dichloromethane (manufacturer: JT Baker, USA). The dispersed phase was sufficiently dissolved by stirring for 30 minutes or more and then used. As the continuous phase was an aqueous solution containing 1% (w/v) polyvinyl alcohol (viscosity: 4.8-5.8 mPa s). A container including 500 mL of the continuous phase was connected to an emulsification apparatus equipped with a membrane having 30 μm diameter pores, while simultaneously injecting the prepared dispersed phase to produce the microspheres in suspension. The resulting microsphere suspension was placed in a preparation vessel and stirred at 200 rpm.

The temperature of the membrane emulsification apparatus and the preparation vessel was maintained at 25° C. When the dispersed phase injection was completed, stirring was maintained for 30 minutes. In this step, 495 mL of the continuous phase was removed, while leaving 5 mL of continuous phase, and the same amount of new continuous phase solution was added. The organic solvent was removed while maintaining the temperature at 45° C. for 3 hours. After removal of the organic solvent, the temperature of the microsphere suspension was lowered to 25° C. The microsphere suspension was washed three times with deionized water to remove residual polyvinyl alcohol, and the microspheres were lyophilized.

Example 7-1: Manufacture of Deslorelin Microspheres 4.4 g of Resomer R203H (manufacturer: Evonik, Germany) and 0.6 g of deslorelin acetate (manufacturer: Chengdu Kaijie Biopharm, China) were mixed with 15.7 g of dichloromethane (manufacturer: JT Baker, USA) and 7.5 g of methyl alcohol (manufactured by Sigma Aldrich, USA) to form a dispersed phase. The dispersed phase was sufficiently dissolved by stirring for 30 minutes or more and then used.

As the continuous phase was an aqueous solution containing 1% (w/v) polyvinyl alcohol (viscosity: 4.8-5.8 mPa·s). A container including 790 mL of the continuous phase was connected to an emulsification apparatus equipped with a membrane having 30 μm diameter pores, while simultaneously injecting the prepared dispersed phase to produce the microspheres in suspension at a flow rate of 5 mL per minute. The resulting microsphere suspension was placed in a preparation vessel and stirred at 180 rpm.

The temperature of the membrane emulsification apparatus and the preparation vessel was maintained at 25° C. When the dispersed phase injection was completed, stirring was maintained for 30 minutes. In this step, 785 mL of the continuous phase was removed, while leaving 5 mL of continuous phase, and the same amount of new continuous phase solution was added. The organic solvent was removed while maintaining the temperature at 40° C. for 3 hours. After removal of the organic solvent, the temperature of the microsphere suspension was lowered to 25° C. The microsphere suspension was washed three times with deionized water to remove residual polyvinyl alcohol, and the microspheres were lyophilized.

Example 7-2: Preparation of a Bupivacaine Microsphere

The dispersed phase was prepared by mixing 4.5 g of Resomer R203H (manufacturer: Evonik, Germany), a biocompatible polymer, and 0.5 g of a bupivacaine base (manufacturer: Dishman, India) in 12 g of dichloromethane (manufacturer: J.T Baker, USA). The dispersed phase was sufficiently dissolved by stirring for 30 minutes or more and then used.

An aqueous solution of 1% (w/v) polyvinyl alcohol (viscosity: 4.8-5.8 mPa·s) was used as a continuous phase. 600 mL of the continuous phase was poured into the preparation vessel equipped with high speed mixer (L4RT, Silverson, UK) and stirred at 4000 rpm, while injecting the dispersed phase at a flow rate of 12 mL per minute and maintaining the temperature of the preparation vessel to be 25° C. When the dispersed phase injection was completed, the suspension in the preparation vessel was maintained to be stirred at 25° C. for 30 minutes.

595 mL of the continuous phase was removed, while leaving 5 mL of continuous phase, and the same amount of new continuous phase solution was added. The organic solvent was removed while maintaining the temperature at 45° C. for 3 hours. After removal of the organic solvent, the temperature of the microsphere suspension was lowered to 25° C. The microsphere suspension was washed three times with deionized water to remove residual polyvinyl alcohol, and the microspheres were lyophilized.

Comparative Example 1: Production of Microspheres Prepared by Using Different Continuous Phase Exchange Time The dispersed phase was prepared by mixing 3.5 g of a biocompatible polymer Resomer R203H (manufacturer: Evonik, Germany) and 1.5 g of donepezil base (manufacturer: Neuland Laboratories, India) with 9.2 g of dichloromethane (manufacturer: J.T Baker, USA). The dispersed phase was sufficiently dissolved by stirring for 30 minutes or more and then used.

An aqueous solution of 1% (w/v) polyvinyl alcohol (viscosity: 4.8-5.8 mPa·s) was used as a continuous phase. A container including 460 mL of the continuous phase was connected to an emulsification apparatus equipped with a membrane having 40 μm diameter pores, while simultaneously injecting the prepared dispersed phase to produce the microspheres in suspension. The resulting microsphere suspension was placed in a preparation vessel and stirred at 150 rpm.

The temperature of the membrane emulsification apparatus and the preparation vessel was maintained at 25° C. When the dispersed phase injection was completed, stirring was maintained for 5 minutes. In this step, 455 mL of the continuous phase was removed, while leaving 5 mL of continuous phase, and the same amount of new continuous phase solution was added. The organic solvent was removed while maintaining the temperature at 451° C. for 3 hours. After removal of the organic solvent, the temperature of the microsphere suspension was lowered to 25° C. The microsphere suspension was washed three times with deionized water to remove residual polyvinyl alcohol, and the microspheres were lyophilized.

Comparative Example 2: Preparation of Microspheres by Using Different Continuous Phase Exchange Amounts 3.5 g of a biocompatible polymer Resomer R203H (manufacturer: Evonik, Germany) and 1.5 g of donepezil base (manufacturer: Neuland Laboratories, India) were mixed with 9.2 g of dichloromethane (manufacturer: J.T Baker, USA) to prepare a dispersed phase. The dispersed phase was sufficiently dissolved by stirring for 30 minutes or more and then used.

An aqueous solution of 1% (w/v) polyvinyl alcohol (viscosity: 4.8-5.8 mPa·s) was used as a continuous phase. A container including 460 mL of the continuous phase was connected to an emulsification apparatus equipped with a membrane having 40 μm diameter pores, while simultaneously injecting the prepared dispersed phase to produce the microspheres in suspension. The resulting microsphere suspension was placed in a preparation vessel and stirred at 150 rpm.

The temperature of the membrane emulsification apparatus and the preparation vessel was maintained at 25° C. When the dispersed phase injection was completed, stirring was maintained for 30 minutes. In this step, all of the continuous phase was removed and 2.5 mL of continuous phase (50 (v/v) % of the microsphere) was contained in the microsphere (i.e., the microsphere exists in hydrated form with the continuous phase), while 460 mL of new continuous phase solution was added. The organic solvent was removed while maintaining the temperature at 45° C. for 3 hours. After removal of the organic solvent, the temperature of the microsphere suspension was lowered to 25° C. The microsphere suspension was washed three times with deionized water to remove residual polyvinyl alcohol, and the microspheres were lyophilized.

Comparative Example 2-1: Preparation of Microspheres Using Different Continuous Phase Exchange Amounts 3.5 g of a biocompatible polymer Resomer R203H (manufacturer: Evonik, Germany) and 1.5 g of donepezil base (manufacturer: Neuland Laboratories, India) were mixed with 9.2 g of dichloromethane (manufacturer: J.T Baker, USA) to form a dispersed phase. The dispersed phase was sufficiently dissolved by stirring for 30 minutes or more and then used. An aqueous solution of 1% (w/v) polyvinyl alcohol (viscosity: 4.8-5.8 mPa·s) was used as a continuous phase. A container including 460 mL of the continuous phase was connected to an emulsification apparatus equipped with a membrane having 40 μm diameter pores, while simultaneously injecting the prepared dispersed phase to produce the microspheres in suspension. The resulting microsphere suspension was placed in a preparation vessel and stirred at 150 rpm.

The temperature of the membrane emulsification apparatus and the preparation vessel was maintained at 25° C. When the dispersed phase injection was completed, stirring was maintained for 30 minutes. In this step, 161 mL (35 (v/v) % of the total continuous phase volume) of the continuous phase was removed, while 460 mL of new continuous phase solution was added. The organic solvent was removed while maintaining the temperature at 45° C. for 3 hours. After removal of the organic solvent, the temperature of the microsphere suspension was lowered to 25° C. The microsphere suspension was washed three times with deionized water to remove residual polyvinyl alcohol, and the microspheres were lyophilized.

Comparative Example 3: Preparation of Microspheres Using a Continuous Phase in which Ethyl Alcohol was Mixed 3.5 g of a biocompatible polymer Resomer R203H (manufacturer: Evonik, Germany) and 1.5 g of donepezil base (manufacturer: Neuland Laboratories, India) were mixed with 9.2 g of dichloromethane (manufacturer: J.T Baker, USA) to form a dispersed phase. The dispersed phase was sufficiently dissolved by stirring for 30 minutes or more and then used.

An aqueous solution comprising 1% (w/v) polyvinyl alcohol (viscosity: 4.8-5.8 mPa·s) and 50 (v/v) % of ethyl alcohol was used as a continuous phase. A container including the continuous phase was connected to an emulsification apparatus equipped with a membrane having 40 μm diameter pores, while simultaneously injecting the prepared dispersed phase to produce the microspheres in suspension. The resulting microsphere suspension was placed in a preparation vessel and stirred at 200 rpm.

The temperature of the membrane emulsification apparatus and the preparation vessel was maintained at 25° C. When the dispersed phase injection was completed, stirring was maintained for 30 minutes. In this step, 455 mL of the continuous phase was removed, while the same amount of a new continuous phase solution was added. The organic solvent was removed while maintaining the temperature at 40° C. for 3 hours. After removal of the organic solvent, the temperature of the microsphere suspension was lowered to 25° C. The microsphere suspension was washed three times with deionized water to remove residual polyvinyl alcohol, and the microspheres were lyophilized.

Comparative Example 4: Preparation of Microspheres with a Process of Continuously Adding and Removing a Continuous Phase The dispersed phase was prepared by 3.5 g of a biocompatible polymer Resomer R203H (manufacturer: Evonik, Germany) and 1.5 g of donepezil base (manufacturer: Neuland Laboratories, India) with 9.2 g of dichloromethane (manufacturer: J.T Baker, USA). The dispersed phase was sufficiently dissolved by stirring for 30 minutes or more and then used.

An aqueous solution of 1% (w/v) polyvinyl alcohol (viscosity: 4.8-5.8 mPa·s) was used as a continuous phase. 460 mL of the continuous phase was poured into the preparation vessel equipped with high speed mixer (L4RT, Silverson, UK) and stirred at 2000 rpm, while injecting the dispersed phase at a flow rate of 10 mL per minute and maintaining the temperature of the preparation vessel to be 25° C. When the dispersed phase injection was completed, the continuous phase was removed from the emulsion at a flow rate of 4.6 mL per minute (1 (v/v) % of total volume of the continuous phase), while a new continuous phase was added into the preparation vessel at the same flow rate of the removal of the continuous phase for 1 hour.

The organic solvent was removed while maintaining the temperature at 45° C. for 3 hours. After removal of the organic solvent, the temperature of the microsphere suspension was lowered to 25° C. The microsphere suspension was washed three times with deionized water to remove residual polyvinyl alcohol, and the microspheres were lyophilized.

Experimental Example 1: Morphological Analysis of Microspheres by Electron Microscope This test was conducted to analyze the morphological characteristics of the prepared microspheres, and the detailed experimental procedure is as follows. 5 mg of microspheres were placed on an aluminum stub with a carbon tape and platinum coated using ION-COATER (COXEM, Korea). The aluminum stub was mounted on a scanning electron microscope (COXEM EM-30, Korea) and morphological characteristics were observed at an accelerating voltage of 15 kV.

As shown in FIG. 1A and FIG. 1B, in Comparative Example 1, the continuous phase exchange time was faster than the surface hardening time of the microspheres, and the microspheres were deformed without maintaining the spherical shape, whereas in Example 1-1, most microspheres were completely spherical. Therefore, it is considered that the continuous phase should be replaced after more than 5 minutes, appropriately after the surface is cured.

As can be seen in FIG. 1(c), it was confirmed that particle shape deformation could occur during the continuous phase exchange process when all the continuous phases were removed. Accordingly, it was confirmed that the particle shape was preserved by removing a certain amount of the continuous phase as in Example 1-1 rather than removing all of the continuous phase.

As shown in FIG. 1d and FIG. 1e, in the case where ethyl alcohol was contained in the continuous phase, in particular, in Example 5, it was predicted that ethyl alcohol increased the dichloromethane solubility to facilitate the removal. On the other hand, in Comparative Example 3, it was confirmed that when 50% (v/v) or more ethyl alcohol was added to the continuous phase, rapid dichloromethane removal resulted in microsphere deformation.

Experimental Example 2: Analysis of Residual Organic Solvent

The following test was carried out to confirm the stability and storage stability of the microspheres by measuring the amount of residual solvent in the microspheres prepared by freeze-drying.

For determination of residual dichloromethane and ethyl acetate, 100 mg of lyophilized microspheres is placed in a volumetric flask, and 10 mL of dimethylformamide is added. The solution is diluted, transferred to a 5 mL vial, and placed in a gas chromatograph equipped with a headspace sampler. And the residual solvent was measured. The column used was DB-624 (manufactured by Agilent, USA) (30 m×0.53 mm, 3 μm), the sample injection amount was 1 μL and the flame ionization detector temperature was set at 250° C.

For measurement of residual methyl alcohol, 100 mg of freeze-dried microspheres were placed in a volumetric flask, 5 mL of N-methylpyrrolidone was added, and the resulting solution was diluted and transferred to a 5 mL vial. The residual solvent was measured with a gas chromatograph equipped with a headspace sampler. The column used was DB-624 (manufactured by Agilent, USA) (30 m×0.53 mm, 3 μm), the sample injection amount was 1 μL and the flame ionization detector temperature was set at 250° C.

For measurement of residual ethyl alcohol, 100 mg of freeze-dried microspheres is placed in a volumetric flask, 5 mL of N-methylpyrrolidone is added thereto, and the resulting solution is diluted and transferred to a 5 mL vial. The residual solvent was measured with a gas chromatograph equipped with a headspace sampler. The column was DB-624 (manufactured by Agilent, USA) (30 m×0.53 mm, 3 μm), the sample injection amount was 1 μL and the flame ionization detector temperature was set at 240° C.

TABLE 1

| | Dichloromethane (ppm) | Ethyl acetate (ppm) | Ethyl alcohol (ppm) | Methyl alcohol (ppm) |
|---|---|---|---|---|
| Example 1 | 508 | — | — | — |
| Example 1-1 | 170 | — | — | — |
| Example 1-2 | 161 | — | — | — |
| Example 2 | 362 | — | — | — |
| Example 3 | — | 106 | — | — |
| Example 4 | 192 | — | — | — |
| Example 4-1 | 196 | — | — | — |
| Example 4-2 | 169 | — | — | — |
| Example 4-3 | 232 | — | — | — |
| Example 4-4 | 316 | — | — | — |
| Example 4-5 | 192 | — | — | — |
| Example 4-6 | 222 | — | — | — |
| Example 4-7 | <10 | — | — | — |
| Example 5 | 163 | — | 65 | — |
| Example 6 | 229 | — | — | — |
| Example 6-1 | 183 | — | — | — |
| Example 6-2 | 201 | — | — | — |
| Example 6-3 | 216 | — | — | — |
| Example 7 | 223 | — | — | — |
| Example 7-1 | 218 | — | — | 173 |
| Example 7-2 | 210 | — | — | — |
| Comparative example 1 | 1210 | — | — | — |
| Comparative example 2 | 195 | — | — | — |
| Comparative example 2-1 | 1642 | — | — | — |
| Comparative example 3 | 151 | — | 32 | — |
| Comparative example 4 | 1745 | — | — | — |

As shown in Table 1, Example 1, Example 1-1, and Comparative Example 1 show the change in the amount of residual dichloromethane depending on the continuous phase exchange time, and after 15 minutes of the continuous phase exchange time, the amount of residual dichloromethane is 600 ppm or less.

As can be seen from the results of Example 1-1, Example 2, and Comparative Example 2, it was confirmed that when the continuous phase was discontinuously exchanged, the residual solvent decreased in proportion to the amount of the continuous phase removal. However, as can be seen from the result of Comparative example 2, wherein all the continuous phases are removed, the microspheres were morphologically deformed by applying pressure to the microspheres. In addition, as in Comparative example 2-1, wherein the continuous phase volume to be exchanged was not sufficient, dichloromethane was not efficiently removed and a large amount of dichloromethane remained. It is preferable to maintain the residual amount of dichloromethane in the microspheres at 1000 ppm or less in order to improve storage stability. Preferably, the residual dichloromethane is maintained at 600 ppm or less.

It has been found that when using a continuous phase comprising ethyl alcohol like Example 5 and Comparative Example 3, the removal of residual dichloromethane is facilitated. As shown in Table 1, Example 6, Example 6-1, Example 6-2, Example 6-3, in which the continuous phase was continuously added and removed, the residual dichloromethane was lowered for a short period of time and appeared to be advantageous for the residual dichloromethane removal. However, it was confirmed that when the amount of the continuous phase to be exchanged was less than 1% (v/v) of the total continuous phase as in Comparative example 4, it was not effective in removing dichloromethane.

As shown in Table 1, it was confirmed that residual solvents were efficiently removed even when organic solvents other than dichloromethane were used as Example 3, Example 5, Example 7-1, and Comparative Example 3.

Experimental Example 3: Accelerated Storage Stability Analysis of Microspheres of the Present Invention In order to confirm the storage stability of the prepared microspheres by comparing the stored microsphere performance under the harsh storage conditions, the following tests were conducted.

Each 1 g of the microspheres of Example 1-1 according to the present invention and the microspheres of Comparative Example 1 were placed in 5 mL vials and stored in an incubator at 40° C. for 14 days and then the average particle size was measured with a particle size analyzer (Microtrac Bluewave, Japan). 50 mg of the microspheres taken out of the incubator was mixed with 1 mL of deionized water, mixed with a vortex mixer for 20 seconds, and dispersed in an ultrasonic generator for 1 minute. The resulting microsphere dispersion was placed in a particle size analyzer and measured for 20 seconds.

The span value as an index of particle size uniformity was obtained by the following equation (1).

Span Value=$(Dv_{0.9}-Dv_{0.1})/Dv_{0.5}$    [Equation 1]

TABLE 2

| | Average particle size before storage | Average particle size after storage (Storage temperature: 40° C.) (Storage period: 14 days) |
|---|---|---|
| Example 1-1 | $Dv_{0.5}$ = 81.5 μm<br>Span Value = 0.63 | $Dv_{0.5}$ = 86.3 μm<br>Span Value = 0.65 |
| Comparative example 1 | $Dv_{0.5}$ = 79.6 μm<br>Span Value = 0.60 | $Dv_{0.5}$ = 381 μm<br>Span Value = 1.72 |

As shown in Table 2, the particle size of Example 1-1 was confirmed to maintain a similar level of particle size after storage at 40° C.

On the other hand, the microspheres of Comparative example 1 were cured at a storage temperature of 40° C., and all of the microspheres were hardly hardened as a whole. After measuring the particle size of the suspended microspheres, it is confirmed that, the mean particle size of the microspheres significantly increased. As a result, it is considered that the residual dichloromethane in the microspheres of Example 1-1 and Comparative Example 1 is a cause of deterioration of the storage stability of the microspheres.

In addition, the span value of Example 1-1 after storage in which the residual solvent was efficiently removed showed a mere 3% increase compared to those before storage, whereas in Comparative example 1 where the residual solvent removal was not efficient, the span value exhibits 286% increase compared to those before storage. Thus, the residual solvent was considered to have adversely affected the morphological characteristics of the microspheres. Therefore, the microsphere with storage stability of the present invention shows 100% or less of change of span value based on the initial span value, preferably, 50% at storage temperature of 40° C. for 14 days.

What is claimed is:

1. A method for preparing biodegradable microspheres comprising:
   (a) forming a biodegradable polymer solution by dissolving a biodegradable polymer alone; or a biodegradable polymer and a drug in an organic solvent;
   (b) uniformly mixing the biodegradable polymer solution prepared in the step (a) with an aqueous solution containing a surfactant, to form an emulsion containing the biodegradable polymer solution as a dispersed phase and an aqueous solution containing the surfactant as a continuous phase;
   (c) extracting and evaporating the organic solvent from the dispersed phase in the emulsion of step (b) to the continuous phase to produce microspheres, wherein a part of the continuous phase containing the extracted organic solvent is removed, while a new continuous phase is supplied; and
   (d) recovering the microspheres from the continuous phase containing the produced microspheres of step (c),
   wherein the part of the continuous phase in step (c) is removed discontinuously or continuously, and
   (i) when discontinuously removing the part of the continuous phase in step (c), the removed continuous phase has a volume ratio of 40% (v/v) to 99% (v/v) based on the total volume of the continuous phase, or has a weight ratio of a remaining continuous phase except for the one time weight ratio of continuous phase of the microparticle in the step (c), or
   (ii) when continuously removing the part of the continuous phase in step (c), the rate of removal of the continuous phase is in the range of 2% (v/v) to 200% (v/v)/min based on the total volume of the continuous phase.

2. The method of claim 1, wherein the biodegradable polymer is one or more selected from the group consisting of polylactide, polyglycolide, poly(lactide-co-glycolide), poly(lactide-co-glycolide) glucose and polycaprolactone.

3. The method of claim 2, wherein the molar ratio of lactic acid to glycolic acid in the poly(lactide-co-glycolide) is 99:1 to 50:50.

4. The method of claim 1, wherein the organic solvent is one or more selected from the group consisting of dichloromethane, chloroform, ethyl acetate, acetone, acetonitrile, dimethyl sulfoxide, dimethylformamide, methyl ethyl ketone, acetic acid, methyl alcohol, ethyl alcohol, propyl alcohol, and a mixture thereof.

5. The method according to claim 1, wherein the aqueous solution containing the surfactant of step (b) comprising
   (i) water, or a mixed solvent comprising water and one or more organic solvent selected from the group consisting of methyl alcohol, ethyl alcohol, propyl alcohol and ethyl acetate as a solvent; and
   (ii) a surfactant.

6. The method according to claim 1, wherein the surfactant in step (b) is one or more selected from the group consisting of methylcellulose, polyvinylpyrrolidone, carboxymethylcellulose, lecithin, gelatin, polyvinylalcohol, polyoxyethylene sorbitan fatty acid ester, polyoxyethylene castor oil derivatives and a mixture thereof.

7. The method according to claim 1, wherein the surfactant of step (b) is in an amount of 0.01% (w/v) to 20% (w/v) based on the total volume of the aqueous solution containing the surfactant.

8. The method according to claim 1, wherein the new aqueous solution containing a surfactant in step (c) is supplied discontinuously or continuously.

9. The method according to claim 1, wherein the step of removing a part of the continuous phase in step (c) and supplying new aqueous solution containing a surfactant starts at 10 to 60 minutes from an initiation of hardening of the microsphere surface.

10. The method of claim 1, wherein the new aqueous solution comprising surfactant of step (c) comprises
    (i) water, or a mixed solvent comprising water and one or more organic solvent selected from a group consisting of methyl alcohol, ethyl alcohol, propyl alcohol and ethyl acetate as a solvent; and
    (ii) a surfactant.

11. The method of claim 10, wherein one or more solvent selected from the group consisting of methyl alcohol, ethyl alcohol and propyl alcohol in the mixed solvent is 0.1% (v/v) to 40% (v/v) based on the total volume of the mixed solvent.

12. The method of claim 1, wherein the removal of the continuous phase and the supply of new aqueous solution containing surfactant in step (c) proceeds simultaneously or asynchronously.

13. The method of claim 1, further comprising a step of filtering and washing between steps (c) and (d).

14. The method of claim 1, further comprising a step of drying the microspheres produced in step (d).

15. The method of claim 1, further comprising a step of filling a container with the microspheres produced in step (d).

16. The method of claim 1, wherein the drug is selected from the group consisting of donepezil, memantine, rivastigmine, entecavir, lamivudine, rotigotine, ropinirole, bupivacaine, ropivacaine, meloxicam, buprenorphine, fentanyl, granisetron, triamcinolone, cytarabine, carmustine, tamsulosin, polmacoxib, testosterone, estradiol, risperidone, paliperidone, olanzapine, aripiprazole, goserelin, leuprolide, triptorelin, buserelin, nafarelin, deslorelin, octreotide, pasireotide, lanreotide, vapreotide, exenatide, liraglutide, lixisenatide, semaglutide and salts thereof.

17. The method of claim 1, wherein the residual solvent content of the microspheres is 600 ppm or less.

* * * * *